United States Patent
Aalsma et al.

(10) Patent No.: US 6,200,317 B1
(45) Date of Patent: Mar. 13, 2001

(54) DEVICE FOR MOVING TWO OBJECTS RELATIVE TO EACH OTHER

(75) Inventors: Arthur Martinus Michael Aalsma, Rotterdam; Hendricus Johannes Grootenboer, Borne; Edsko Evert Geert Hekman, Enschede; Jouwert Wilhelm Jacobus Lucas Stapert, Maastricht, all of (NL)

(73) Assignee: Universiteit Twente and Technologiestichting STW, Utrecht (NL)

( * ) Notice: Subject to any disclaimer, the term of this patent is extended or adjusted under 35 U.S.C. 154(b) by 0 days.

(21) Appl. No.: 09/331,673

(22) PCT Filed: Dec. 17, 1997

(86) PCT No.: PCT/NL97/00706

§ 371 Date: Sep. 23, 1999

§ 102(e) Date: Sep. 23, 1999

(87) PCT Pub. No.: WO98/27885

PCT Pub. Date: Jul. 2, 1998

(30) Foreign Application Priority Data

Dec. 23, 1996 (NL) .................................................. 1004873

(51) Int. Cl.[7] .................................................. A61B 17/56
(52) U.S. Cl. .............................. 606/62; 606/63; 606/86; 606/57; 606/105; 606/58
(58) Field of Search .................................. 606/62, 63, 67, 606/68, 69, 72, 73, 74, 75, 76, 77, 78, 79, 105

(56) References Cited

U.S. PATENT DOCUMENTS

| 4,262,665 | * | 4/1981 | Roalstad et al. ........................ 606/62 |
| 5,415,660 | * | 5/1995 | Campbell et al. ...................... 606/62 |
| 5,704,938 | * | 1/1998 | Staehlin et al. ........................ 606/62 |

FOREIGN PATENT DOCUMENTS

| 2726460 | | 11/1994 | (FR) . |
| 6-343276 | * | 12/1994 | (JP) ........................................ 606/62 |
| WO 90/15928 | | 12/1990 | (WO) . |

OTHER PUBLICATIONS

Patent Abstracts of Japan, vol. 95, No. 3, Apr. 28, 1995; JP 06 343276.

* cited by examiner

*Primary Examiner*—Pedro Philogene
(74) *Attorney, Agent, or Firm*—Dorsey & Whitney LLP

(57) ABSTRACT

A device for moving a first object relative to a second object, which device comprises a first part, which can be fixed to the first object, and a second part, which can be fixed to the second object. The first part comprises an elongated portion, along which the second part can move, which second part is provided with a clamping member, which is capable of clampingly engaging the elongated portion. The clamping member comprises shape memory metal, which gives the clamping member a clamping shape or a releasing (non-clamping) shape, depending on the temperature of the shape memory metal. The device may be suitable for being implanted into a human or animal body, whereby the first object is a first bone portion and the second object is a second bone portion, which bone portions are to be moved relative to each other.

14 Claims, 3 Drawing Sheets

DEVICE FOR MOVING TWO OBJECTS RELATIVE TO EACH OTHER

BACKGROUND OF THE INVENTION

1. Field of the Invention

The invention relates to a device for moving a first object relative to a second object, which device comprises a first part, which can be fixed to said first object, and a second part, which can be fixed to said second object. Such a device may be used for moving bone portions relative to each other inside a human or animal body, whereby said first object is a first bone portion and said second object is a second bone portion.

Although the invention is not limited to medical applications, the present specification will describe the implementation of the invention for the movement of bone portions relative to each other inside a human body.

2. Description of Related Art

Devices are known wherein two bone portions are connected by means of pins to an elongation apparatus present outside the body, which moves the pins in such a manner that the desired movement is effected at the desired speed of the bone portions. One drawback of such external fixation devices is that they constitute a considerable physical and psychological burden for the patient, and that there is moreover a constant risk of infection in several places where the skin is pierced by pins.

Furthermore devices are known which can be implanted into the human body and which comprise a drive motor which moves the two bone portions to the desired extent relative to each other. Such a device is known from U.S. Pat. No. 5,415,660, which publication describes an elongation pin comprising two ends, which are each fixed to a bone portion, whilst the elongation pin is capable of telescoping out, thus elongating the pin. The drive motor used for said elongation thereby consists of a shape memory metal, whose shape is dependent on the temperature, as will be explained in more detail as yet.

A device for moving bone portions relative to each other, which is to be implanted into the body, must exhibit a high degree of reliability, which can be achieved by reducing the number of parts to a minimum. In addition to that the device must have small dimensions. Furthermore it may be necessary that the device is capable not only of moving the two bone portions in a direction away from each other, but also towards each other to a desired extent. The latter may for example be important if, for whatever reason, the bone portions have been moved too much or when it becomes necessary at a certain point in time to release or reverse the load being exerted on the tissue of the human body.

SUMMARY OF THE INVENTION

The object of the invention is to provide a device for moving objects such as bone portions relative to each other, which device exhibits a high degree of reliability, which is capable of generating large forces, and which is capable of moving the two objects both towards each other and away from each other.

In order to accomplish that objective the device is according to the invention provided with a first part comprising an elongated portion, along which the second part can move, which second part is provided with a clamping member, which is capable of clampingly engaging said elongated portion, and which comprises shape memory metal which gives the clamping member a clamping shape or a releasing (non-clamping) shape, depending on the temperature of the shape memory metal. Preferably the device is suitable for being implanted into a human or animal body, whereby said first object is a first bone portion and said second object is a second bone portion.

In one preferred embodiment said second part is provided with a first clamping member and with a second clamping member, which are each capable of clampingly engaging the elongated portion of said first part of the device some distance apart, whereby both clamping members comprise shape memory metal.

Shape memory metal is an alloy which may exhibit various phases, depending on the temperature. Such shape memory metal may for example consist of a TiNi alloy. The temperature ranges of the various phases are separated by a transition range. Said transition range can be adjusted to the desired value, for example round 37° C., the temperature of the human body, by a suitable selection of the composition and the treatment of the material. The phase above the transition range is the austenitic phase, and the phase below the transition range is the martensitic phase of the shape memory metal. A shape memory metal alloy can be produced and treated (trained) in such a manner that the material attempts to take a certain shape upon being heated to the austenitic phase. In addition to that it can be treated in such a manner that it attempts to take a different shape upon being cooled to the martensitic phase. The deformation may amount to several per cent. The term shape memory metal used herein is understood to mean the above-described bidirectional shape memory metal.

If the deformation is prevented or opposed by external means, high stresses will develop in the material, so that large forces can be exerted by the material. The stress that is developed is greatest in the austenitic phase, since the material has the highest modulus of elasticity in that phase.

By manufacturing the clamping members from shape memory metal it becomes possible to have a clamping member engage the elongated portion of the first part of the device at any random location, whereby the clamping member blocks relative movement of the first and the second part of the device in either direction.

In one preferred embodiment the elongated portion is substantially bar-shaped, and the clamping member is substantially ring-shaped, with said elongated portion being clampingly or releasingly surrounded by said clamping member. The ring-shaped clamping member thereby comprises an opening, through which the bar-shaped elongated portion, which is for example configured as a round pin, extends. Said opening has a particular dimension which depends on the temperature of the shape memory metal from which the ring is made, when the dimension is small, the bar-shaped portion is clamped down, and when the dimension is large, the ring encloses the bar-shaped portion with some play.

Preferably the first clamping member has its releasing shape at a particular temperature, namely the body temperature, whilst the second clamping member has its clamping shape at that temperature. As a result of that there will always be eon clamping member to perform its clamping action during the period that the device is present in the body, without being energized to do so.

The shape memory metal of each of the clamping members may be trained in such a manner that when the temperature rises above body temperature, the first clamping member whilst change from a releasing shape into a clamping shape, whilst the second clamping member will change from a clamping shape into a releasing shape. Both clamping members may thereby be provided with a heating element, which may be selectively energized.

In another preferred embodiment the clamping shape of the first clamping member is obtained by heating said member from the body temperature to a higher temperature, whilst the releasing shape of the second clamping member is obtained by cooling said clamping member from the body temperature to a lower temperature. The clamping action of a clamping member always takes place in the austenitic phase thereby, in which phase the shape memory metal has a high modulus of elasticity. The heating of the shape memory metal from the body temperature to a higher temperature may take place in various manners. In one preferred embodiment said heating takes place by passing electric current through the metal.

In another preferred embodiment said heating takes place by means of a resistance foil, which completely or partially envelopes the shape memory metal. Said resistance foil generates heat when electric current is passed therethrough. The foil may be provided with an insulating layer on the outside, so that the generated heat can only escape to a limited extent, and consequently slowly, to the tissue present outside the resistance foil. The cooling of the shape memory metal from the body temperature to a lower temperature can be effected by means of one or more Peltier elements, which are known per se and which operate as a semiconductor heat pump. Said Peltier elements may also be used as heating elements when the polarity at the connecting points is reversed.

The use in accordance with the invention of a clamping member made of a shape memory metal makes it possible to fix the two parts of the device in any position relative to each other, and to use a device of small dimensions, whereby the first part substantially consists of a thin round bar, whilst the second part, which surrounds said bar, may also be designed to have small dimensions.

According to another aspect of the invention the second part is provided with two clamping members, which are connected together by a connecting member comprising shape memory metal, which is capable of giving the connecting member an elongated or a short form, depending on the temperature of the shape memory metal. In the elongated form the distance between the clamping members is larger than in the short form. It is thereby preferred for the connecting member to have its elongated form when the temperature of the shape memory metal is higher than the temperature of the connecting member in its short form, which latter temperature is preferably the body temperature.

Preferably the device is provided with one or more rechargeable batteries for energizing the heating elements and/or cooling elements that are provided. The energy for charging the batteries can be supplied from outside the body by exciting a primary coil present outside the body, which coil passes energy by means of an electromagnetic field to a secondary coil present in the device inside the body. The batteries are thereby used for energy storage in order to be capable of supplying the relatively large amount of energy required for energizing the various parts of the device.

Furthermore control means are present for controlling the energizing of the various parts of the device from a location outside the body, whereby the communication between the control means inside the body and those outside the body can likewise take place via said primary and secondary coils. Said communication may also be effected by radiographic means or by other known means. In another preferred embodiment said control means have been implanted into the body together with the first part and the second part of the device, so that the control of the device takes place inside the body, which control may be programmed or initiated by signals from outside the body.

The rechargeable batteries and/or the control means are preferably incorporated in the second part, in which the members to be heated or cooled are present, so that said members can be readily connected together.

Preferably the device is designed such that the entire device, including the batteries that may be provided and/or the control means, can be implanted into the marrow of a bone.

The invention furthermore relates to a method for moving two objects relative to each other, wherein a first part of a device, which first part comprises an elongated portion, is fixed to one object and a second part of the device is fixed to the other object, which second part is moved along said elongated part, whereby it clampingly engages said elongated portion at different locations by means of a clamping member comprising shape memory metal, which shape memory metal is heated and/or cooled in order to give said clamping member a clamping or a releasing shape.

Further aspects of the invention, which may be used separately and/or in combination with each other, will be described hereafter by means of an embodiment and be defined in the claims.

BRIEF DESCRIPTION OF THE DRAWINGS

Hereafter an embodiment of a device for moving bone portions relative to each other will be described by way of illustration with reference to the drawing.

The figures are merely diagrammatic illustrations, wherein like parts are numbered alike.

DETAILED DESCRIPTION OF THE INVENTION

Figure 1:
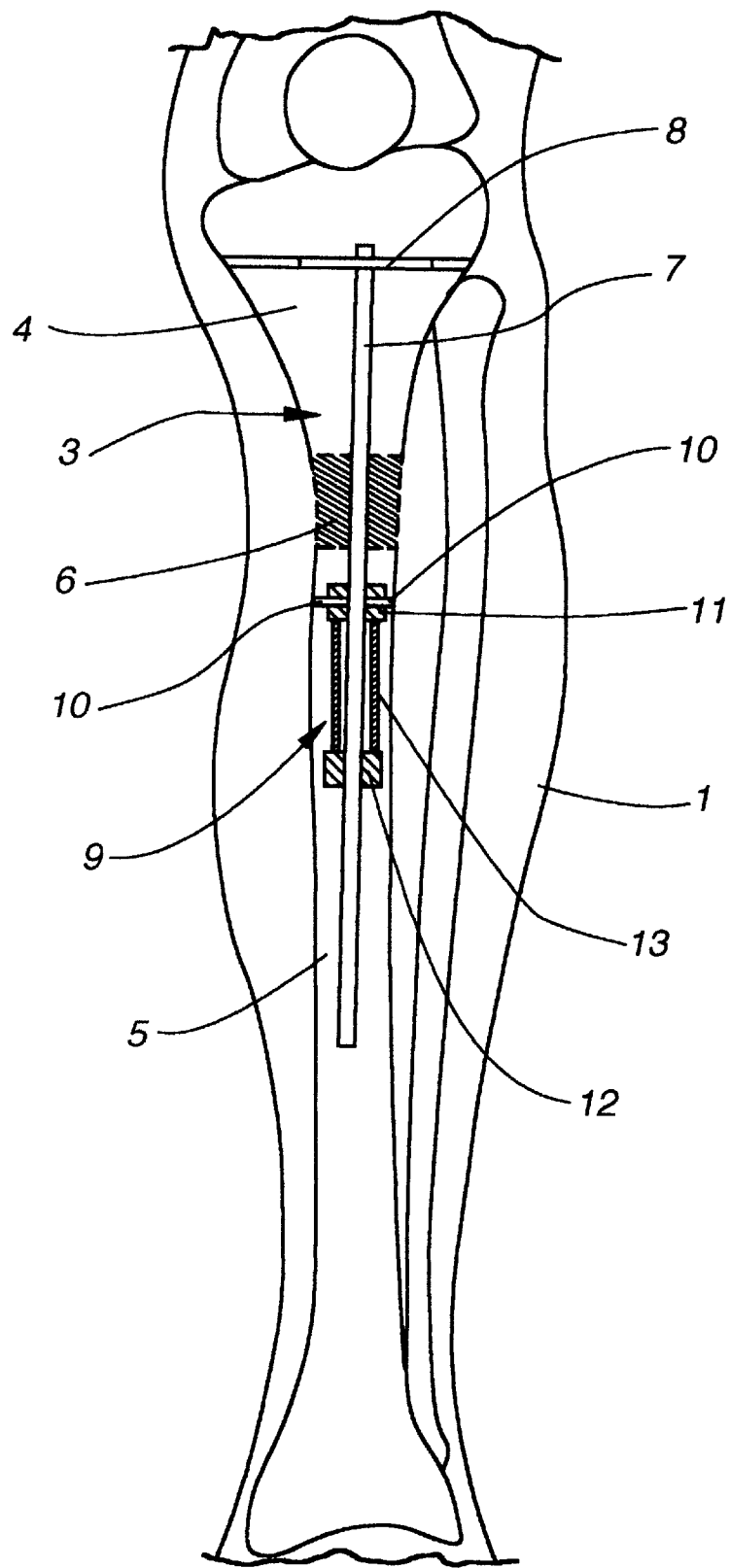
FIG. 1 is a longitudinal section of a human lower leg, into which an elongation pin has been placed.

FIG. 1 shows a human lower leg 1, in which a number of bones are present, with one bone 4, 5 being provided with an elongation pin 3. Said elongation pin 3 has been fitted in order to elongate bone 4, 5 by moving first bone portion 4 and second bone portion 5, which together form bone 4, 5, apart in small steps at regular intervals for a certain period of time. Said moving apart of the two bone portions 4, 5 is possible because bone 4, 5 has been separated into two parts (sawn through) so as to form bone portions 4, 5.

When the two bone portions 4, 5 are moved apart, a tissue 6 will form between said bone portions 4, 5, which tissue 6 will grow during the time the two bone portions 4, 5 are being moved relative to each other. Once the two bone portions 4, 5 are no longer moved relative to each other, tissue 6 will change with time from an elastic tissue into a harder tissue, which connects the two bone portions 4, 5 together. In this manner bone 4, 5 can be elongated.

The relative movement of the bone portions 4, 5 is effected by a device which has been implanted into the bone, which device consists of a first part 7, which is substantially comprised of a metal, round bar, which is connected to first bone portion 4 by means of a fixing pin 8, whereby said metal bar 7 extends to inside second bone portion 5. The second part 9 of the device is fixed in second bone portion 5 by means of fixing pins 10, with second part 9 surrounding bar 7.

Second part 9 of the device consists of a first clamping member 11 and a second clamping member 12, which are each capable of clampingly engaging bar 7. The two clamping members 11, 12 are interconnected by means of a tubular connecting member 13. Said connecting member 13 may be fixed to clamping members 11, 12 by means of a glued connection, a welded connection or a clamped connection, for example.

In FIG. 1 first clamping member 11 is connected to second bone portion 5. In a preferred embodiment, however, second clamping member 12 is connected to second bone portion 5, as a result of which the forces occurring in second part 9 of the device will predominantly be pressure forces.

Figure 2:
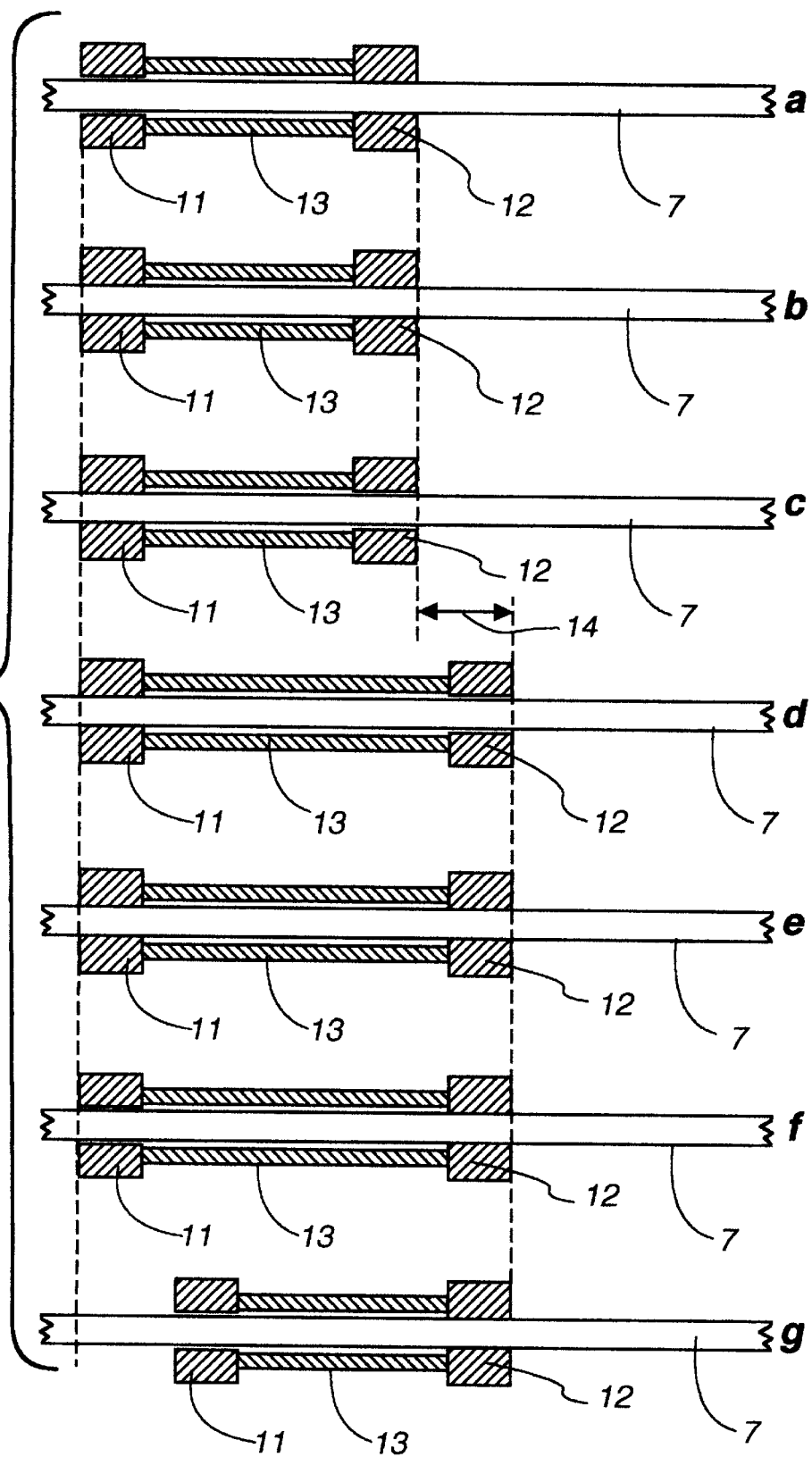
FIG. 2 shows the operation of the elongation pin.

FIG. 2 shows the manner in which second part 9 of the device can move along bar 7 of said first part. Ring-shaped first clamping member 11, tubular connecting member 13 and ring-shaped second clamping member 12 are shown in sectional view in FIG. 2. Clamping members 11, 12 as well as connecting member 13 are made of shape memory metal, namely a TiNi-alloy. The shape memory metal of first clamping member 11 is composed and trained in such a manner that the dimension of the hole in the ring at the body temperature of 37° C. is such that bar 7 is not clamped down, whilst the shape of first clamping member 11 at a higher temperature, for example at 55° C., is such that said clamping member clamps down on bar 7.

The composition and the training of the shape memory metal of second clamping member 12 is such that the second clamping member clamps down on bar 7 at the body temperature of 37° C. The releasing shape of second clamping member 12 is obtained by cooling the shape memory metal of clamping member 12 down to a temperature of about 15° C.

The composition and the training of the shape memory metal of tubular connecting member 13 is such that the length of said connecting member at the body temperature of 37° C. is less than at a higher temperature, for example 55° C. The difference in length may amount to about 2 per cent, so that an elongation of 1 mm can be achieved with an overall length of 50 mm.

Situations a–g in FIG. 2 show the successive conditions of second part 9 of the device. In situation a the temperature of the shape memory metal of each of the members 11, 12, 13 is the same as the body temperature of 37° C. This is likewise the case in situation g, but in situation g second member 11, 12, 13 has moved relative to bar 7 over a distance indicated by arrow 14. Said movement along bar 7 is illustrated in situations b–f.

In situation b first clamping member 11 is heated until it clampingly engages bar 7. Then, as is indicated in situation c, second clamping member 12 is cooled until it has its releasing shape, in which condition it no longer clampingly engages bar 7, therefore. Then, as is indicated in situation d, connecting member 13 is heated to body temperature again, so that said clamping member 12 clampingly engages bar 7. After first clamping member 11 has subsequently cooled down to body temperature, so that it no longer clampingly engages bar 7 (situation L), also connecting member 13 is cooled down to body temperature, resulting in situation g, which corresponds with situation a, with this difference that second part 11, 12, 13 of the device has been moved a distance 14 relative to bar 7.

Figure 3:
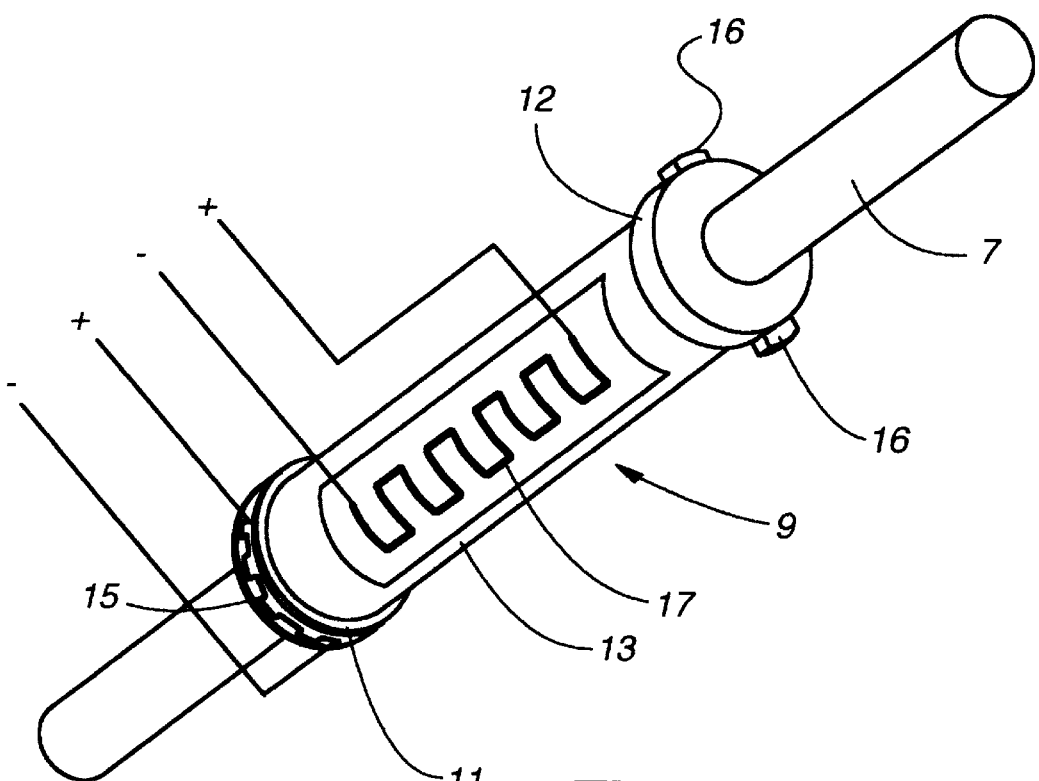
FIG. 3 is a perspective view of a part of said elongation pin.

FIG. 3 is a perspective view of a part of bar 7 and second part 9 of the device. Ring-shaped first member 11 is enveloped by a resistance foil 15, which is indicated diagrammatically, as are the connecting points for the current supply for heating the resistance foil. Ring-shaped second member 12 is provided with two Peltier elements 16, which are capable of cooling the shape memory metal of clamping member 12 when current is being supplied to said Peltier elements. The number of Peltier elements may also be larger than two. In that case they will act as a heat pump, whereby heat is discharged from the shape memory metal of clamping member 12 to the surroundings thereof. In this manner the shape memory metal of clamping member 12 can be cooled relative to the ambient temperature, which is the same as the body temperature of 37° C.

Tubular connecting member 13, which is positioned between the two clamping members 11, 12, is enveloped by a resistance foil diagrammatically indicated by block-shaped line 17, which can be heated by supplying current thereto.

In order to increase the amount of friction between clamping members 11, 12 and bar 7 and/or to effect a certain heat insulation between clamping member 11, 12 and bar 7, the inside of the clamping member abutting against bar 7, and/or the surface of bar 7 may be provided with a special heat-insulating and/or friction-increasing coating.

Figure 4:
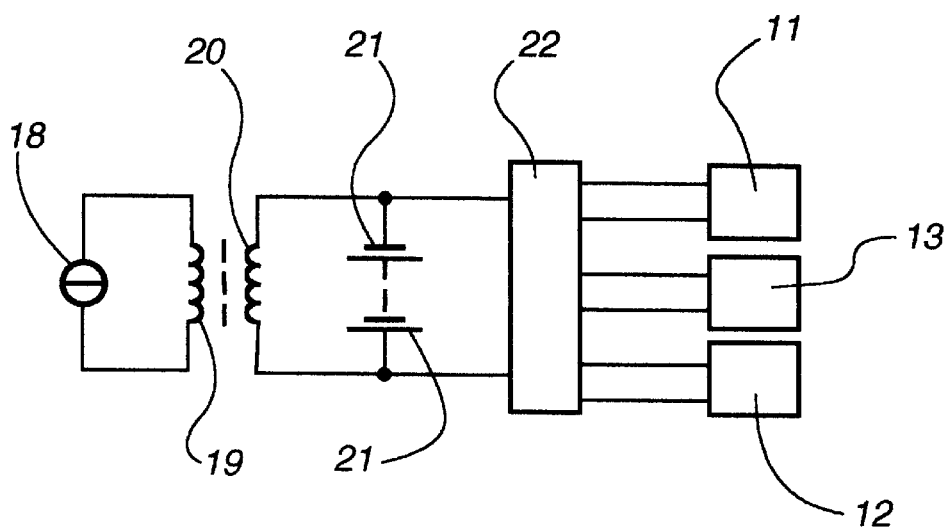
FIG. 4 shows the energizing of the various parts of the elongation pin.

FIG. 4 shows the energy supply of the device. Electric power supply 18 is connected to a primary coil 19, which is for example provided round the patient's lower leg. Primary coil 19 is capable of transmitting energy, by means of an electromagnetic field, to secondary coil 20, which is capable of charging the two batteries 21. This makes it possible to feed a relatively large amount of energy to the device during a short period of time, whilst said electric energy can be transported to the device over a much longer period.

Block 22 indicates the control unit of the device, which unit is controlled by a control device present outside the body, which is in communication with control unit 22, for example by means of radio waves. Said control unit 22 is capable of transmitting electric energy to the (diagrammatically indicated) clamping members 11, 12 and connecting member 13, so that the shape memory metal of each of said members can be selectively heated (clamping member 11 and connecting member 13) or cooled (clamping member 12).

The illustrated embodiment of the device should be considered as a mere example, the invention may also be embodied in different manners.

What is claimed is:

1. A device for moving a first object relative to a second object, said device comprising a first part fixed to said first object and a second part fixed to said second object, said first part comprising a centrally disposed elongated rod-like portion, along which said second part can move, said second part being provided with a clamping member disposed about said elongated portion for engaging said elongated portion and which comprises shape memory metal for giving said clamping member a clamping shape or a releasing shape depending on the temperature of the shape memory metal.

2. A device according to claim 1, wherein said device is suitable for implanting into a human or animal body, and wherein that said first object is a first bone portion and said second object is a second bone portion.

3. A device according to claim 1 wherein said second part includes a first clamping member and a second clamping member, each capable of clampingly engaging the elongated portion of said first part of said device some distance apart, whereby both clamping members comprise shape memory metal.

4. A device according to claim 3, wherein the temperature at which said first clamping number realizes a releasing shape is the same temperature at which said second clamping member realizes a clamping shape.

5. A device according to claim 4, wherein said first clamping member realizes a clamping shape at a higher temperature than the temperature at which said second clamping member realizes a clamping shape.

6. A device according to claim 4, wherein said second clamping member has a releasing shape at a lower temperature than the temperature at which said first clamping member realizes a releasing shape.

7. A device according to claim 1, wherein said elongated portion is substantially bar-shaped, said clamping member is substantially ring-shaped and surrounds said elongated portion.

8. A device according to claim 1, wherein said second part includes two clamping members connected together by a connecting member comprising shape memory metal capable of giving said connecting member an elongated or a short form depending on the temperature of the shape of memory metal, wherein the distance between said clamping members is greater when said connecting member realizes the elongated form than the distance between said clamping members when said connecting member realizes the short form.

9. A device according to claim 8, wherein said connecting member surrounds said elongated portion of said first part and includes a ring-shaped clamping member at both ends.

10. A device according to claim 1, further comprising a heating or cooling means for heating or cooling said clamping members or said connecting member, and also comprising a separate energy supply unit for supplying energy to said heating or cooling means.

11. A device according to claim 10, wherein said energy supply unit comprises a rechargeable battery.

12. A device according to claim 10, further comprising a control means for controlling said heating and/or cooling means.

13. A method for moving two objects relative to each other with a relative movement device comprising a first part including a centrally disposed elongated rod-like portion and a second part including a clamping member disposed about said elongated portion comprising shape memory metal which can be heated or cooled to yield a clamping shape or a releasing shape so as to clamp onto or release from said elongated portion of said first part, said method comprising the steps of:

a. affixing said first part to one object and affixing said second part to the other object;
   b. clamping said clamping member onto said elongated portion at a first location;
   c. heating said clamping member to form a releasing shape thereby releasing said clamping member from said elongated portion;
   d. moving said second part relative to said first part; and
   e. cooling said clamping member to form a clamping shape thereby clamping said clamping member to said elongated portion at a second location spaced apart from said first location.

14. The method according to claim 13, wherein step (c) comprises cooling said clamping member to form a releasing shape, and wherein step (e) comprises heating said clamping member to form a clamping shape.

* * * * *